(12) United States Patent
Rogers

(10) Patent No.: US 9,358,238 B2
(45) Date of Patent: Jun. 7, 2016

(54) METHOD OF ENHANCING THE PERFORMANCE OF BROILER CHICKENS

(71) Applicant: Intervet Inc., Madison, NJ (US)

(72) Inventor: John A. Rogers, Hendersonville, NC (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/675,864

(22) Filed: Apr. 1, 2015

(65) Prior Publication Data

US 2015/0202209 A1    Jul. 23, 2015

Related U.S. Application Data

(63) Continuation of application No. 13/896,475, filed on May 17, 2013, now abandoned.

(60) Provisional application No. 61/648,793, filed on May 18, 2012.

(51) Int. Cl.
*A61K 31/55* (2006.01)
*A23K 1/18* (2006.01)
*A23K 1/16* (2006.01)

(52) U.S. Cl.
CPC . *A61K 31/55* (2013.01); *A23K 1/16* (2013.01); *A23K 1/1628* (2013.01); *A23K 1/1826* (2013.01)

(58) Field of Classification Search
CPC .................................................. A61K 31/55
See application file for complete search history.

(56) References Cited

U.S. PATENT DOCUMENTS

| 4,585,770 | A | 4/1986 | Frechet et al. |
| 4,900,735 | A | 2/1990 | Grandadam |
| 5,731,028 | A | 3/1998 | Chevremont et al. |
| 5,847,124 | A | 12/1998 | Chevremont et al. |
| 7,207,289 | B2 | 4/2007 | Montgomery |
| 2013/0109673 | A1 | 5/2013 | Dubuis et al. |

FOREIGN PATENT DOCUMENTS

| AU | 2012200318 A1 | 2/2012 |
| WO | 2008006828 A1 | 1/2008 |
| WO | 2008092924 A1 | 8/2008 |
| WO | 2009073756 A1 | 6/2009 |

OTHER PUBLICATIONS

Jones, K.W., "Protein Lipid Interactions in Processed Meats", Reciprocal Meat Conference Proceedings, 1984, pp. 52-56, vol. 37.
Kheiri et al., "Effects of Supplemental Ractopamine and L-carnitine on growth performance, blood biochemical paprameters and carcass traits of male broiler chicks", African Journal of Biotechnology, 2011, pp. 15450-15455, vol. 10(68).
Mersmann, H. J., "Overview of the effects of beta-adrenergic receptor agonists on animal growth including mechanisms of action", J. Animal Science, 1998, pp. 160-172, vol. 76.
PCT International Search Report for corresponding PCT Application No. PCT/EP2013/060249, mailed Jul. 4, 2013, (3 pages).
Towhidi, et al., "Effect of different levels of zilpaterol hydrochloride on growth performance and carcass characteristics of male japanese quails", The 3rd International Conference on Sustainable Agriculture for Developing Countries, Jul. 26-29, 2011, p. 210.
Towhidi, et al., "Effect of skip a day feeding zilpaterol hydrochloride on growth performance in broiler chicken", The 3rd International Conference on Sustainable Agriculture for Developing Countries, Jul. 26-29, 2011, p. 211.
Ricks, C.A., Use of repartitioning agents to improve performance and body composition of meat animals, Reciprocal Meat Conference Proceedings, 1984, pp. 5-11, 37, National Live Stock and Meat Board, Chicago.

*Primary Examiner* — Zohreh Fay

(57) ABSTRACT

A method of enhancing the performance of chicken comprising administering zilpaterol to the chicken wherein the concentration of zilpaterol is from about 1 ppm to about 13 ppm and is administered every day for a period of about 7 to about 21 days.

11 Claims, 6 Drawing Sheets

Figure 1: Average Daily Gain of Broilers Fed Various Levels of Zilpaterol for 7 or 14 Days
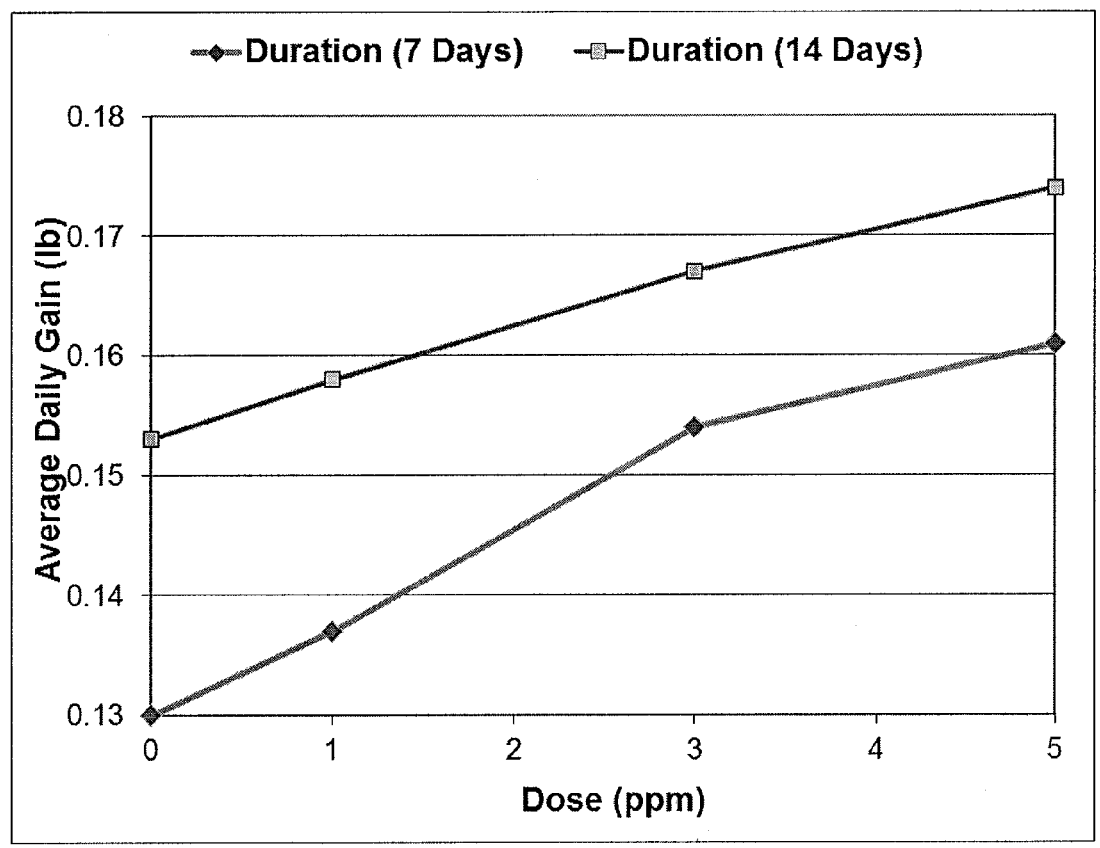

Figure 2: Feed Efficiency of Broilers Fed Various Levels of Zilpaterol for 7 or 14 Days
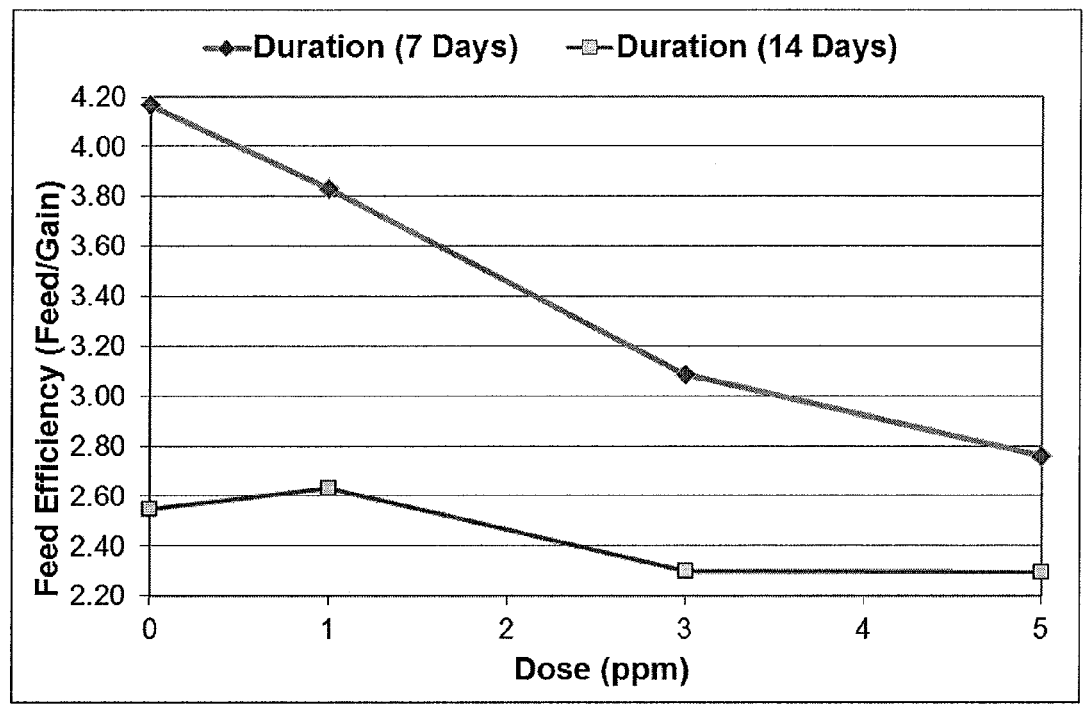

Figure 3: Carcass Yield of Broilers Fed Various Levels of Zilpaterol for 7 or 14 Days
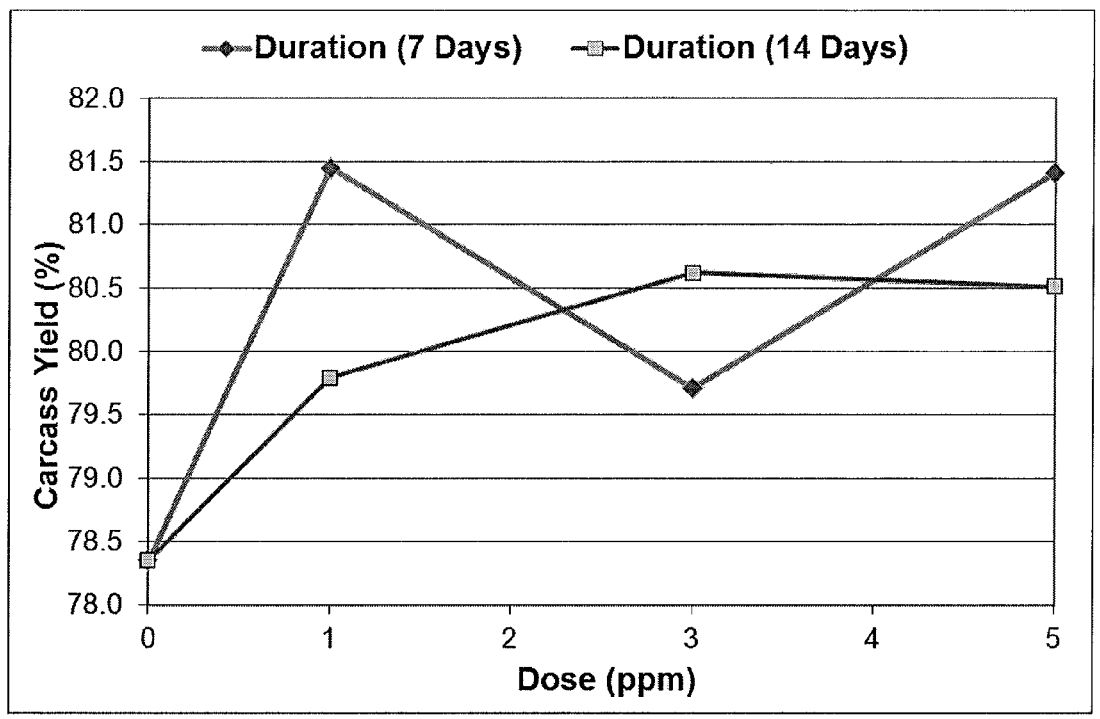

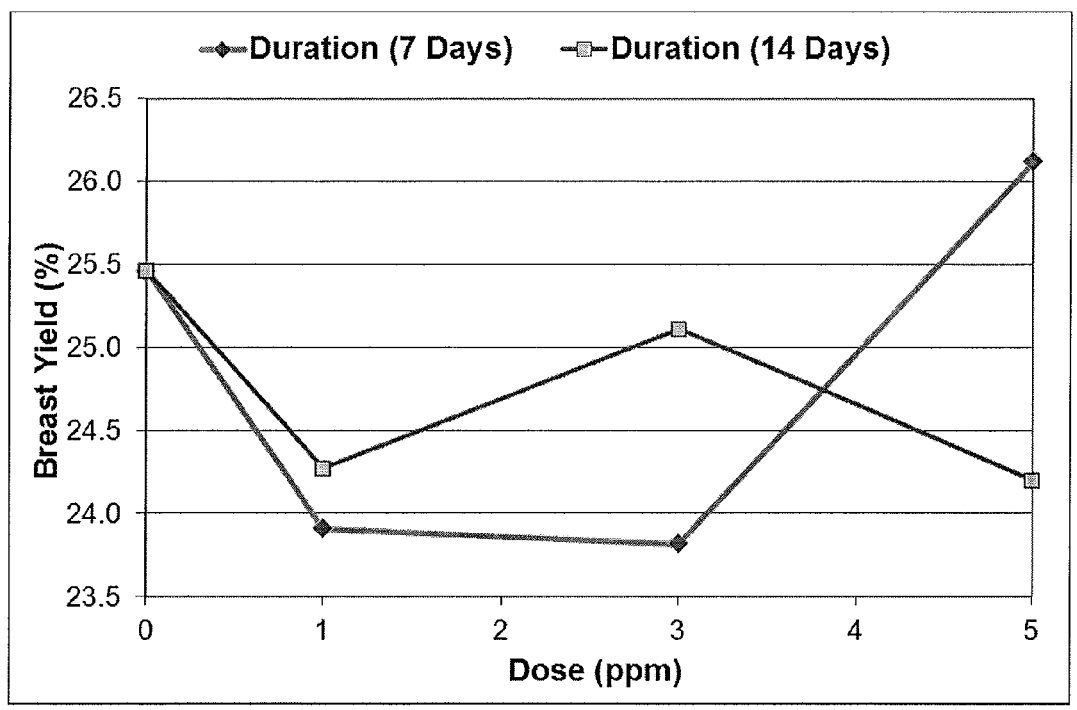
Figure 4: Breast Yield of Broilers Fed Various Levels of Zilpaterol for 7 or 14 Days Figure 5: Breast Weight of Broilers Fed Various Levels of Zilpaterol for 7 or 14 Days
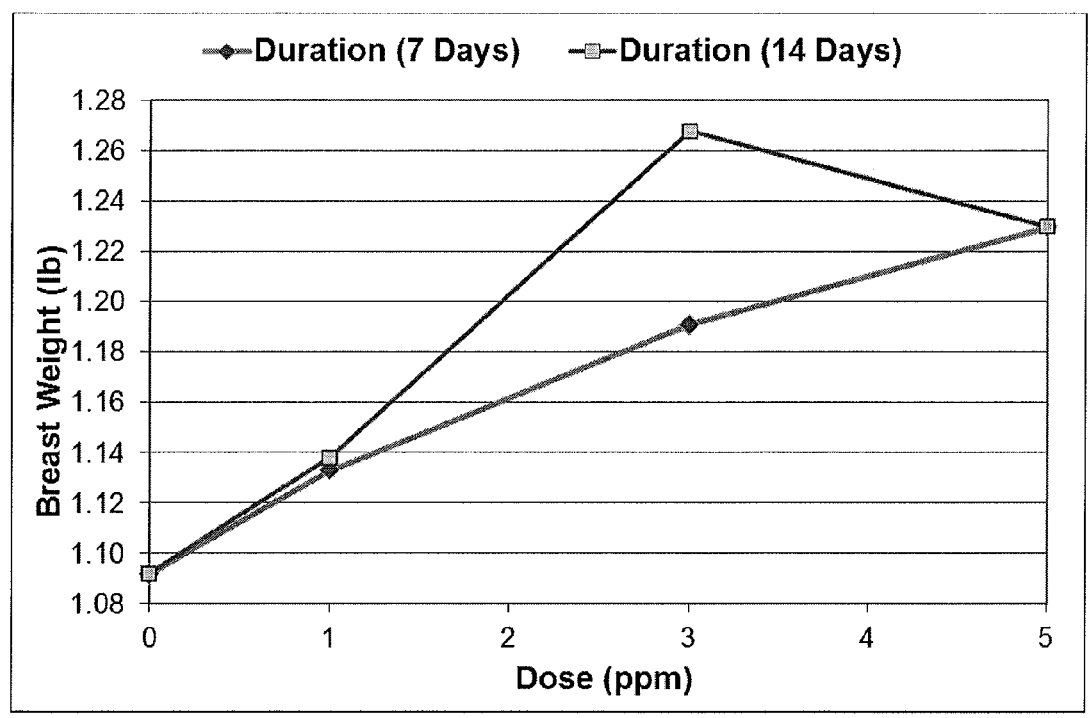

Figure 6: Body Weight on Day 42 of Broilers Fed Various Levels of Zilpaterol for 7 or 14 Days
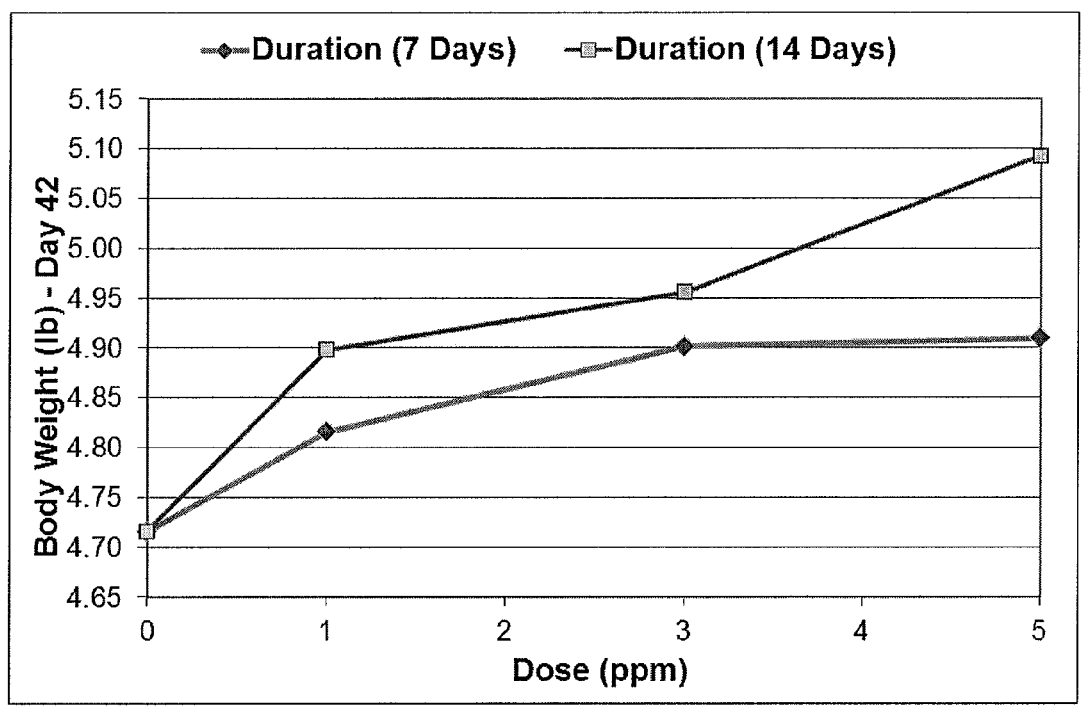

METHOD OF ENHANCING THE PERFORMANCE OF BROILER CHICKENS

CROSS-REFERENCE TO RELATED APPLICATIONS

This application is a continuation application of co-pending U.S. application Ser. No. 13/896,475, filed May 17, 2013, that claims priority under 35 U.S.C. §119(e) of provisional application U.S. Ser. No. 61/648,793 filed May 18, 2012, the contents of both of which are hereby incorporated by reference in their entireties.

BACKGROUND OF THE INVENTION

Zilpaterol is a known adrenergic β-2 agonist corresponding in structure to Formula (I):

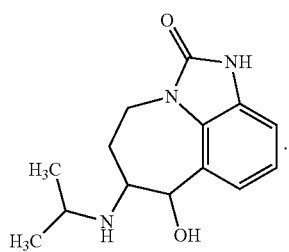

The IUPAC name for zilpaterol is 4,5,6,7-tetrahydro-7-hydroxy-6-(isopropylamino) imidazo[4,5,1-jk]-[1]benzazepin-2(1H)-one. The Chemical Abstracts name for zilpaterol is 4,5,6,7-tetrahydro-7-hydroxy-6-[(1-methyl-ethyl)amino]-imidazo[4,5,1-jk][1]benzazepin-2(1H)-one.

Zilpaterol hydrochloride is sold by Merck Animal Health, under the trademark ZILMAX®. It is approved in the United States for increased rate of weight gain, improved feed efficiency, and increased carcass leanness in cattle fed in confinement for slaughter during the last 20 to 40 days on feed. The approved inclusion rate of zilpaterol hydrochloride is 6.8 grams/ton (7.5 ppm) in feed. In U.S. Pat. No. 4,585,770, Fréchet et al. discuss compounds, such as zilpaterol, encompassed by a genus characterized as 6-amino-7-hydroxy-4,5,6,7-tetrahydro-imidazo[4,5,1-j-k][1]-benzazepin-2-(1H)-one derivatives and acid addition salts thereof. Fréchet et al. state that such compounds may be used as an active ingredient for inducing antihypertensive and hypotensive activity in a warm-blooded animal.

In U.S. Pat. No. 4,900,735, Grandadam discusses a zootechnical composition comprising zilpaterol and acid addition salts thereof. Grandadam states that such a composition may be used in general to increase the weight of cattle, pigs, sheep, and poultry.

In U.S. Pat. Nos. 5,731,028 and 5,847,124, Chevremont et al. discuss crystallized anhydrous zilpaterol hydrochloride, and particularly crystallized anhydrous zilpaterol hydrochloride wherein less than 5% of the crystals have a size of less than 15 µm, and at least 95% of the crystals have a size of less than 250 µm. According to Chevremont et al., such crystals may be incorporated into animal feed to increase body weight and meat quality. Chevremont et al. provide methods for making such crystals, and discuss using the crystals to make animal premixes in which the crystals are secured to a corn cob support having a greater particle size. They also discuss monohydrate and trihydrate intermediates that can be useful in, for example, making the crystals.

In U.S. Pat. No. 7,207,289, Montgomery discusses methods for increasing beef production, reducing feed intake while maintaining beef production, and reducing incidences of liver abscess in cattle. These methods comprise administering a feed comprising an ionophore and macrolide antibiotic during an initial period, and then administering a feed comprising zilpaterol (including zilpaterol hydrochloride) with essentially no ionophore or macrolide antibiotic.

In WO 2008/006828, Miculka, et al. disclose zilpaterol enantiomers compositions and methods of making and using such compositions to increase rate of weight gain, improve feed efficiency and increase carcass leanness in livestock, poultry and fish. In WO 2008/092924, Alemna-Perea et al. disclose enantioselective synthesis of zilpaterol and intermediates.

Ricks et al., (Reciprocal Meat Conference Proceedings, Vol. 37, 1984) disclose broiler chickens when fed the beta-agonist Clenbuterol at 1 ppm for 18 days (28 to 46 days of age) showed performance improvements in average daily gain (ADG) and feed efficiency (FE) of 3.3% to 3.0% respectively, above controls.

Mersmann, (1998, Journal of Animal Science, 76:160-172) summarized previous literature regarding the feeding of beta agonists to mammals and birds and suggested that the magnitude of effect of feeding beta agonists for growth promotion in chickens was lower (~2% improvement) compared to other species. Beta agonists disclosed were norepinephrine, epinephrine, cimeterol, ractopamine, L.664.969 and salbutmol. The explanation provided for this low response, and generally accepted by the industry, was that some species (e.g., broiler chickens) have been intensely selected for growth rate and therefore has less potential to increase growth because they are closer to the biological maximal growth rate.

Kheiri, et al. (African Journal of Biotechnology, 2011, Vol. 10(68), pp 15450-15455) discloses the effect of the beta agonist ractopamine as a growth promoter of broiler chickens. Three levels of ractopamine were fed to broiler chickens from 3 to 6 weeks of age, 0, 5 and 10 mg/kg). The results indicate that daily body weight gain, feed intake, and feed conversion were not significantly affected by the administration of ractopamine to broiler chickens.

Towhidi, et al. (The 3rd International Conference on Sustainable Agriculture for Developing Countries, Jul. 26-29, 2011, pg 210) disclose that zilpaterol supplementation of feed for Japanese quails resulted in improved feed conversion ratio but there was not a significant difference in weight gain, final body weight, feed intake and carcass, thigh, breast liver and carcass weight. Birds were fed at zilpaterol levels of 0, 0.2, 0.225, 0.25 mg/kg of live body weight for a 21 day feeding study with birds at 26 days of age.

Towhidi, et al. (The $3^{rd}$ International Conference on Sustainable Agriculture for Developing Countries, Jul. 26-29, 2011, pg 211) disclose the improved feed efficiency of chickens feed zilpaterol in a skip a day manner. Birds were fed at zilpaterol levels of 0, 0.2, 0.25, 0.3 mg/kg of live body weight for a 20 day feeding trial beginning at 25 days of age.

SUMMARY OF THE INVENTION

In an embodiment, the invention is a method of decreasing the length of time required for a chicken to reach market weight comprising feeding zilpaterol to the chicken wherein the concentration of zilpaterol is from about 1 ppm to about 13 ppm and is administered every day.

In another embodiment, the time required to reach market weight is decreased from about 42 days to about 35 days of age. In yet another embodiment, the time required to reach market weight is decreased by 2 days or 3 days or 4 days or 5 days or 6 days or 7 days.

In an embodiment, the invention is a method of increasing the body weight of a chicken comprising feeding zilpaterol to the chicken wherein the concentration of zilpaterol is from about 1 ppm to about 13 ppm and is administered every day.

In another embodiment, the invention is a method of improving the average daily gain (ADG) of a chicken comprising feeding zilpaterol to the chicken wherein the concentration of zilpaterol is from about 1 ppm to about 13 ppm and is administered every day.

In another embodiment, the invention is a method of improving the feed efficiency (FE) of a chicken comprising feeding zilpaterol to the chicken wherein the concentration of zilpaterol is from about 1 ppm to about 13 ppm and is administered every day.

In another embodiment, the invention is a method of improving the carcass yield of a chicken comprising feeding zilpaterol to the chicken wherein the concentration of zilpaterol is from about 1 ppm to about 13 ppm and is administered every day.

In another embodiment, the invention is a method of improving the breast weight of a chicken comprising feeding zilpaterol to the chicken wherein the concentration of zilpaterol is from about 1 ppm to about 13 ppm and is administered every day.

In another embodiment, the invention is a method of improving the composition (increase muscle protein and/or decreased abdominal fat content) of the carcass wherein the concentration of zilpaterol is from about 1 ppm to about 13 ppm and is administered every day.

In another embodiment, the invention is a method of improving the uniformity of the size of the carcass and/or various cuts of meat wherein the concentration of zilpaterol is from about 1 ppm to about 13 ppm and is administered every day.

In yet another embodiment, the zilpaterol is administered for a period of about 7 days to about 21 days. In further embodiments, the administration period is about 7 days, or 14 days or 21 days.

In further embodiments, the administration period begins on about 21 days of age, begins on about 28 days of age, or begins on about 35 days of age.

In additional embodiments, the concentration of zilpaterol is about 1 ppm, about 2 ppm, about 3 ppm, about 4 ppm, about 5 ppm, about 6 ppm, about 7 ppm, about 8 ppm, about 9 ppm, about 10 ppm, about 11 ppm, about 12 ppm, or about 13 ppm.

In additional embodiments, the concentration of zilpaterol is from about 1 ppm to about 13 ppm, from about 1 ppm to about 5 ppm, from about 1 ppm to about 7 ppm, from about 2 to 5 ppm, from about 2 ppm to about 7 ppm, from about 3 ppm to about 7 ppm, from about 3 ppm to about 9 ppm, from about 5 ppm to about 9 ppm, from about 5 ppm to about 11 ppm, from about 7 ppm to about 11 ppm or about 7 ppm to about 13 ppm.

In one embodiment, the zilpaterol is administered via the feed.

In another embodiment, the zilpaterol is administered via the drinking water. The concentration in drinking water is adapted to deliver the equivalent amount of zilpaterol per chicken as when administered in feed.

In an embodiment, the zilpaterol is zilpaterol hydrochloride.

BRIEF DESCRIPTION OF THE FIGURES

FIG. 1 shows the average daily gain of broilers fed at various levels of zilpaterol for 7 or 14 days.

FIG. 2 shows the feed efficiency of broilers fed various levels of zilpaterol for 7 or 14 days.

FIG. 3 shows carcass yield of broilers fed various levels of zilpaterol for 7 or 14 days.

FIG. 4 shows breast yield of broilers fed various levels of zilpaterol for 7 or 14 days.

FIG. 5 shows breast weight of broilers fed various levels of zilpaterol for 7 or 14 days.

FIG. 6 shows body weight on day 42 of broilers fed various levels of zilpaterol for 7 or 14 days.

DETAILED DESCRIPTION OF THE INVENTION

Demand for poultry meat has consistently increased at around three times the rate of population growth over each of the past five decades, according to the United Nations' Food and Agriculture Organisation (FAO). In order to meet this increasing demand both more efficient production of meat and greater effectiveness of resource utilization in poultry operations would be necessary.

Enhancing animal growth or feed efficiency can have substantial impact on the poultry meat industry by reducing the high cost of feeding and maintaining food-producing animals, thus directly improving profitability. For example, in the poultry industry, even a slight increase in broiler growth rate coupled with improved feed efficiency brings the broiler chicken to market maturity faster at a lower cost. With more than 3.6 billion broilers raised annually just in the United States, significant savings are realized for even small or incremental enhancements in the animal's growth and/or efficiency.

The present invention encompasses methods of decreasing the length of time required for a chicken to reach market weight. This leads to a more efficient use of the animal facilities and reduces the resources (e.g. energy) needed to produce chicken meat. The present invention encompasses further methods and formulations for enhancing growth and/or feed efficiency in broiler chickens by zilpaterol. Additionally, methods are provided for enhancing carcass weight yield and breast weight in broiler chickens using zilpaterol. Furthermore, methods and formulations for improving the amount of (high value) edible tissue (such as breast meat) produced are provided.

Zilpaterol is preferably used as zilpaterol hydrochloride. Zilpaterol can be used both as a racemate and as single enantiomer. Zilpaterol may be orally administered by a variety of methods, but is preferably included in the feed or drinking water of the broiler chicken. The effective concentration of zilpaterol is from 1 ppm to about 13 ppm in feed or drinking water. The dose can also be expressed as mg/kg bodyweight of the animal/day.

These amounts are to be administered normally every day (daily) for 7-21 days or for a substantial portion of the life of the animal.

In the method according to the current invention, zilpaterol is administered every day (daily) to the chicken. Administration in the context of the invention includes the availability of the zilpaterol in the feed or drinking water of the chicken either ad libitum or in the form of batch feeding. Such a daily administration includes continuous administration i.e. during the administration period zilpaterol is included in all feed (or drinking water) that is offered to the broiler chicken for consumption or zilpaterol is included in at least one feed or feeding component that is fed to the chicken continuously during the whole zilpaterol administration period.

In one embodiment, the duration of zilpaterol administration (zilpaterol administration period) is 7 days. In another embodiment, the duration of zilpaterol administration is 14 days. In another embodiment, the duration of zilpaterol administration is 21 days.

In one embodiment, the administration of zilpaterol starts on 21 days of age. In another embodiment, the administration of zilpaterol starts on 28 days of age. In another embodiment, the administration of zilpaterol starts on 35 days of age.

Zilpaterol is administered every day from 35 to 42 days of age. In another embodiment, zilpaterol is administered every day from 28 to 35 days of age. In yet another embodiment, zilpaterol is administered from 21 to 28 days of age.

Zilpaterol is administered every day from 35 to 49 days of age. In another embodiment, zilpaterol is administered every day from 28 to 42 days of age. In yet another embodiment, zilpaterol is administered from 21 to 35 days of age.

Zilpaterol is administered every day from 35 to 56 days of age. In another embodiment, zilpaterol is administered every day from 21 to 42 days of age. In yet another embodiment, zilpaterol is administered from 28 to 49 days of age.

In further embodiments, the administration period begins on day 35 of age and the zilpaterol is administered for about 7 days.

In other embodiments, the administration period begins on day 28 of age and the zilpaterol is administered for about 7 days or about 14 days.

In other embodiments, the administration period begins on day 21 of age and the zilpaterol is administered for about 7 days, about 14 days or about 21 days.

For distribution purposes, an admixture of a high concentration of zilpaterol can be prepared in a suitable premix (e.g., Type A Medicated Article) to be included in the feed. The premix is distributed to the end users in bags containing said premix. The end-user, usually the farmer/commercial producer raising poultry, will further dilute the premix into the regular feed that is used for said poultry.

Said premix may contain zilpaterol (e.g., 0.1% to 5%) in diluents. The premix promotes a uniform distribution of the active ingredients in the finished feed into which the premix is blended. It thus performs an important function by ensuring proper distribution of the active ingredient throughout the feed offered to poultry.

As diluents a variety of common solid carriers may be used (e.g., cereal by-products, such as wheat flour, wheat bran or de-oiled rice bran, but also corn meal, alfalfa meal, calcium carbonate, soybean meal, cottonseed oil meal, linseed oil meal, sodium chloride, cane molasses, bone meal, corncob meal, rice kernel, and the like).

If desired, such concentrates or premixes may contain other ingredients, such as minerals, trace elements, or vitamins.

Such concentrates or premixes are then added to the feed of the animal in an amount sufficient to provide the desired concentration in the resulting feed mixture and to provide the desired dosage amounts in the range previously described by suitably mixing with the feed. The known methods of formulating, mixing, and processing feeds which are normally used in the animal feed arts are entirely appropriate for manufacturing feeds containing zilpaterol.

Poultry feed, especially chicken broiler feed, for use in the method of the present invention contains zilpaterol in a concentration of from about 1 ppm to about 13 ppm. In a preferred embodiment, the medicated poultry feed generally contains from 0.9 to 11.8 grams zilpaterol per ton of feed.

The total consumption of zilpaterol will be decreased or increased with changes in the feed inclusion of zilpaterol and with changes in the duration of the treatment period. It is common and it may be found advantageous to change the feed inclusion of zilpaterol during the treatment period and all changes in the concentrations administered to the animals will of course influence the total consumption per animal of active ingredient.

Of importance is that the feed to the animal contain proteins (or essential amino acids, e.g. lysine) and energy in the appropriate proportion, the presence of which in feed is a well-known prerequisite for muscle growth in all species. The dietary protein and energy requirements for various species are well known for those skilled in the art. As an example, a maize-soybean meal diet can be used for broiler chicken, wherein the crude protein and energy concentration should preferably not be less than NRC requirements or current industry practices.

However, increased growth rate may be further increased by feeding a higher dietary crude protein concentration and/or including certain amino acids that are known to be rate-limiting (e.g., lysine) for growth. Similarly, other amounts and proportions of various other nutrients (sufficient energy, minerals, vitamins, etc.) will be required to support optimal muscle growth and/or feed efficiency. In another embodiment, the methods of the invention further comprise administration of greater than normal amounts of protein or essential amino acids.

The compositions and methods of this invention may further include, in combination with zilpaterol, one or more other active ingredients. Other active ingredients include any material which can be added to the feed or drinking water to enhance the animal's performance, health, and/or well-being. Examples of such include anticoccidials such as amprolium, clopidol, decoquinate, diclazuril, halofuginone hydrobromide, lasalocid, monensin, narasin, nicarbazin, robenidine, salinomycin, semduramycin, sulfadimethoxine/ormetoprime, zoalene, and feed additives (i.e., antibiotics and ionophores) used for improved performance such as, bacitracin, bambermycin, chlortetracycline, lincomycin, neomycin, oxytetracycline, penicillin, roxarsone, tylosin, and virginiamycin, enzymes, minerals, vitamins and other supplements. The above active ingredients are also used for various health related concerns. The person skilled in the art will recognize that the agents listed above are examples of a wide range of feed additives which may be used. Other examples are referred to in "2012 Feed Additive Compendium" and "Handbook of Feed Additives 2012".

DEFINITIONS

"Growth" and "enhancing growth" are terms generally known in the art and refer to increases in either, or both, weight and size (e.g., height, width, diameter, circumference, etc.) over that which would otherwise occur without implementation of the methods and/or administration of the compositions of the present invention. Growth can refer to an increase in the mass (e.g., weight or size) of the entire animal or of a particular tissue (e.g., muscle tissue in general or a specific muscle). Alternatively, growth can indicate a relative increase in the mass of one tissue in relation to another, in particular, an increase in muscle tissue relative to other tissues (e.g., adipose tissue).

"Feed efficiency" refers to: feed consumed (lbs)/total live body weight (lbs). "Adjusted Feed efficiency" refers to feed consumed (lbs)/(total live body weight (lbs)+body weight (lbs) of mortalities).

"Average daily gain" refers to body weight gain (lbs)/number of days.

"Breast weight" refers to breast weight (lbs) at slaughter.

"Carcass yield" refers to carcass weight (lbs)/live body weight (lbs)×100.

"Breast yield" refers to breast weight (lbs)/live body weight (lbs)×100.

"Uniformity" refers to the consistency of the size of the carcass and various cuts of meat (i.e. breasts, thighs and etc.).

"ppm" is an abbreviation of parts per million. ppm is a value that represents the part of a whole number in units of 1/1000000. "ppm' is dimensionless quantity, a ratio of 2 quantities of the same unit. For example, a 5 ppm concentration of zilpaterol means 5 mg of zilpaterol per 1 kg of feed.

"Poultry" are domesticated birds kept by humans for the purpose of producing eggs, meat, and/or breeding stock. These most typically are members of the superorder Galloanserae (fowl), especially the order Galliformes (which includes chickens, quails and turkeys) and the family Anatidae (in order Anseriformes), commonly known as "waterfowl" (e.g. domestic ducks and domestic geese). Poultry also includes other birds which are killed for their meat, such as pigeons or doves or birds considered to be game, like pheasants. Chickens (*Gallus gallusdomesticus*) are domesticated fowl.

"Broiler" or "Broiler chickens" are chickens raised for meat production. In most countries the broiler chickens are raised in big operations, housing thousands of animals on an industrial scale.

"Market weight" refers to the body weight of the chicken that is acceptable to be sold. In some markets (e.g. US), broiler chickens are typically 4-6 pounds. In other markets, broilers may range less than 4 lbs or greater than 6. In some markets, larger chickens are called roaster or roaster chickens and typically weigh 5-7 lbs or 6-8 lbs. Chickens of about 4-6 lbs normally reach their market weight in about 42 days. Heavier broiler chickens, 6-8 lbs, can take longer to reach their market weight, for example about 50-56 days.

Other definitions for selected terms used herein will be found within the description of the invention and apply throughout. Unless otherwise defined, all other scientific and technical terms used herein have the same meaning as commonly understood by individuals who are skilled in the art.

EXPERIMENTAL

Example 1

Broiler chickens were fed zilpaterol every day at 1 ppm from day 8 until day 56 of age. The observed zilpaterol performance response was relatively small. In this study, non significant performance increases in Average Daily Gain (ADG) of 1.3-2.6% and Feed Efficiency (FE) of 0.6%-1.9% were reported. However, carcass yield was significantly improved ($P<0.01$) compared to control by 2% when zilpaterol was fed daily at 1 ppm for 7 weeks.

Example 2

Zilpaterol hydrochloride was fed to broiler chickens in a 42 day floor pen study to evaluate the performance response of zilpaterol compared to a non-medicated control group. Six zilpaterol treatment groups consisted of three concentration levels (1, 3, and 5 ppm) and two feeding durations (7 and 14 days) and were administered in feed plus a non medicated control group. A total of 1,680 broiler chickens were allocated by sex to 56 pens with 30 birds/pen, and 4 pens/sex/group (240 birds/group). The 7 day zilpaterol treatments began at day 35 and continued to day 42 of age. The 14 day zilpaterol treatments began at day 28 and continued until day 42 of age. The mean pre-treatment body weight among all groups (six zilpaterol treated groups and control group) were not significantly different.

Post-treatment, there were no statistically significant 2-way or 3-way interactions of sex with duration of treatment and concentration; therefore pooled results over sex are discussed. A summary of the performance response of broiler chickens fed various levels for zilpaterol (0, 1, 3, 5, ppm) and feeding durations (7, 14 days) compared to the control are shown in the following table:

TABLE 1

Performance Response of Broilers Fed Various Levels of Zilpaterol for 7 or 14 Days

| Variable | Duration (Days) | Zilpaterol (ppm) | | | | SE | Improvement (%) | | |
|---|---|---|---|---|---|---|---|---|---|
| | | 0 | 1 | 3 | 5 | | 0 vs 1 | 0 vs 3 | 0 vs 5 |
| Average Daily Gain | 7 | 0.130 | 0.137 | 0.154 | 0.161 | 0.0088 | 5.4% | 18.5% | 23.8% |
| (lb) | 14 | 0.153 | 0.158 | 0.167 | 0.174 | 0.0051 | 3.3% | 9.2% | 13.7% |
| Feed Efficiency (FE) | 7 | 4.166 | 3.831 | 3.085 | 2.760 | 0.3055 | 8.0% | 25.9% | 33.7% |
| (Feed/Gain Ratio) | 14 | 2.548 | 2.632 | 2.301 | 2.295 | 0.0962 | 3.3% | 9.7% | 9.9% |
| Carcass Yield | 7 | 78.35 | 81.45 | 79.71 | 81.41 | 0.9125 | 4.0% | 1.7% | 3.9% |
| (%) | 14 | | 79.79 | 80.62 | 80.51 | | 1.8% | 2.9% | 2.8% |
| Breast Weight | 7 | 1.092 | 1.133 | 1.191 | 1.230 | 0.0672 | 3.8% | 9.1% | 12.6% |
| (lb) | 14 | | 1.138 | 1.268 | 1.230 | | 4.2% | 16.1% | 12.6% |
| Body Weight (lb) | 7 | 4.716 | 4.816 | 4.902 | 4.910 | 0.0699 | 2.1% | 3.9% | 4.1% |
| Day 42 | 14 | | 4.898 | 4.956 | 5.093 | | 3.9% | 5.1% | 8.0% |

The results from this study demonstrated that zilpaterol can significantly improve the performance of broiler chickens. The zilpaterol performance response was very large compared to the control group.

Experimental Design

A total of 1,680 broiler chickens (Cobb 500 strain) were allocated by sex to 56 pens (28 pens of males, 28 pens of females) with 30 birds per pen according to a randomized complete block design during a 42 day study. The six zilpaterol treatment groups were in a 2×3 factorial arrangement with two feeding durations of 7 or 14 days (i.e., days 35-42 or 28-42 respectively) and three zilpaterol concentration levels of 1, 3, or 5 ppm plus an un-supplemented (negative) control group. Treatment groups were randomly assigned by sex to pens within each block.

Average Daily Gain (ADG)

ADG increased as the zilpaterol concentration increased during both feeding durations (7 and 14 day). For the 7 day duration, ADG was significantly (p<0.05) increased with the two highest zilpaterol concentrations (3 and 5 ppm) compared to the controls. An increase in ADG was also observed when zilpaterol was fed for 14 days at 3 ppm and 5 ppm (p=0.0572 and p=0.0047) respectively (see Table 2 and FIG. 1).

Feed Efficiency (FE)

For the 7 day duration, FE (feed/gain) was significantly improved (p<0.05) with the two highest zilpaterol concentrations (3 and 5 ppm) compared to the controls. Similar improvements in FE for the 14 day duration were observed with zilpaterol at these same (3 and 5 ppm) concentration levels (see Table 3 and FIG. 2).

TABLE 3

Feed Efficiency of Broilers Fed Various Levels of Zilpaterol for 7 or 14 Days

| Variable | Duration | Zilpaterol (ppm) | | | | SE | P value | | |
|---|---|---|---|---|---|---|---|---|---|
| | | 0 | 1 | 3 | 5 | | 0 vs 1 | 0 vs 3 | 0 vs 5 |
| Feed Efficiency | 7 | 4.166 | 3.831 | 3.085 | 2.760 | 0.3055 | 0.4430 | 0.0164 | 0.0022 |
| (Feed/Gain) | 14 | 2.548 | 2.632 | 2.301 | 2.295 | 0.0962 | 0.5231 | 0.0647 | 0.0584 |

Mortality

Very low mortality occurred during the study. A total of 52 mortalities (3.10%) occurred during the treatment period (days 28-42). Feeding zilpaterol at any level (1, 3, 5 ppm) had no significant effect on the mean mortality rates compared to the control group for either feeding duration (7 or 14 day).

Carcass Yield and Breast Yield

Zilpaterol significantly (p<0.05) increased carcass yield at the highest zilpaterol 5 ppm concentration (7 and 14 day duration) compared to the control group. A similar significant (p<0.05) increase in carcass yield was observed at the zilpaterol 1 ppm (7 day duration) and zilpaterol 3 ppm (14 day duration) concentrations. For breast yield, there were no statistically significant differences in the zilpaterol treatment groups (average: 24.57%) compared to the control group (25.46%), but two zilpaterol treatment groups (1 and 3 ppm, 7 day duration) tended to have a slightly lower breast yield.

TABLE 2

Average Daily Gain of Broilers Fed Various Levels of Zilpaterol for 7 or 14 Days

| Variable | Duration | Zilpaterol (ppm) | | | | SE | P value | | |
|---|---|---|---|---|---|---|---|---|---|
| | | 0 | 1 | 3 | 5 | | 0 vs 1 | 0 vs 3 | 0 vs 5 |
| Average Daily | 7 | 0.130 | 0.137 | 0.154 | 0.161 | 0.0088 | 0.5719 | 0.0458 | 0.0108 |
| Gain (lb/day) | 14 | 0.153 | 0.158 | 0.167 | 0.174 | 0.0051 | 0.4948 | 0.0572 | 0.0047 |

TABLE 4

Carcass and Breast Yield of Broilers Fed Various Levels of Zilpaterol for 7 or 14 Days

| Variable | Duration | Zilpaterol (ppm) | | | | SE | P Value | | |
| --- | --- | --- | --- | --- | --- | --- | --- | --- | --- |
| | | 0 | 1 | 3 | 5 | | 0 vs 1 | 0 vs 3 | 0 vs 5 |
| Carcass Yield, % | 7 | 78.35 | 81.45 | 79.71 | 81.41 | 0.9125 | 0.0030 | 0.1716 | 0.0034 |
| | 14 | 78.35 | 79.79 | 80.62 | 80.51 | | 0.1497 | 0.0254 | 0.0328 |
| Breast Yield, % | 7 | 25.46 | 23.91 | 23.82 | 26.12 | 1.0894 | 0.0895 | 0.0744 | 0.4576 |
| | 14 | 25.46 | 24.27 | 25.11 | 24.20 | | 0.1891 | 0.6966 | 0.1654 |

The zilpaterol treatment effect relationship between concentration and duration (i.e., total dose basis), using the treatment means from the above table, on carcass and breast yield is shown in FIGS. 3 and 4.

Breast Weight

The overall zilpaterol effect of producing a larger final body weight on day 42 (see next section), combined with a higher carcass yield (%), but with similar (or possibly slightly lower) breast yield (%) resulted in higher breast weight. This effect was significant (p<0.05) at the zilpaterol 3 ppm concentration level for day 14 duration. At the zilpaterol 5 ppm concentration when fed for 7 and 14 days, an increase in breast weight was also observed but at slightly higher level of significance (p=0.5070 and p=0.0580, respectively).

The higher breast weight observed with feeding zilpaterol is consistent with its know effect on metabolism of muscle and fat tissues to modify the normal utilization of nutrients and energy to produce more muscle and less adipose tissue. Although carcass leanness (percent carcass protein) was not specifically measured in this study, the increased breast weight observed with feeding zilpaterol suggests that an increase in muscle synthesis may have occurred. Also, although carcass fat content (e.g., abdominal fat pad) was not measured, the known effect of feeding zilpaterol suggests that a reduction in fat deposition may have occurred. These changes may lead to improvements in uniformity (size) of the carcass and various cuts of meat. See Table 5 and FIG. 5.

Body Weight (Day 21-42)

The final body weight of the controls (4.7 lb) was above the commercial minimum target of a 4.5 lb bird within 42 days, confirming that an acceptable growth rate was achieved during the floor pen study. Zilpaterol significantly (p<0.05) increased final body weight (day 42), particularly at the higher concentrations (3 ppm and 5 ppm) with the longer (14 day) feeding duration compared to the control group. The other zilpaterol treatment groups (lower concentration levels and shorter zilpaterol feeding duration) were also supportive that increasing levels of zilpaterol increased final body weight as shown by the table below.

TABLE 6

Body Weight on Day 42 of Broilers Fed Various Levels of Zilpaterol for 7 or 14 Days

| Variable | Duration | Zilpaterol (ppm) | | | | SE | P Value | | |
| --- | --- | --- | --- | --- | --- | --- | --- | --- | --- |
| | | 0 | 1 | 3 | 5 | | 0 vs 1 | 0 vs 3 | 0 vs 5 |
| Body Weight (lb), Day 42 | 7 | 4.716 | 4.816 | 4.902 | 4.910 | 0.0699 | 0.3179 | 0.0672 | 0.0562 |
| | 14 | 4.716 | 4.898 | 4.956 | 5.093 | | 0.0732 | 0.0196 | 0.0005 |

The large body weight increase (0.38 lb) noted above with zilpaterol (Z5-14d) versus controls (Z0-0d) indicates that the length of time required for broilers to meet their target market weight can be reduced. Based upon the ADG of zilpaterol (Table 2, Z5-14d), the time to reach the target market weight can be reduced by approximately 2 days (0.38 lb/0.174 lb/day).

The zilpaterol treatment effect relationship between concentration and duration (i.e., total dose basis), using the treatment means from the above table, on final body weight (day 42) is shown in Table 6 and FIG. 6.

The increased final body weight observed with zilpaterol compared to the control group with broiler chickens in the above table and FIG. 6 by the magnitude demonstrated in this study was unexpected.

Example 3

Zilpaterol hydrochloride is fed to broiler chickens in a 42 day floor pen study as above in Example 2 with the following exceptions. There are zilpaterol treatment groups for seven

TABLE 5

Breast Weight of Broilers Fed Various Levels of Zilpaterol for 7 or 14 Days

| Variable | Duration | Zilpaterol (ppm) | | | | SE | P Value | | |
| --- | --- | --- | --- | --- | --- | --- | --- | --- | --- |
| | | 0 | 1 | 3 | 5 | | 0 vs 1 | 0 vs 3 | 0 vs 5 |
| Breast Weight, lb | 7 | 1.092 | 1.133 | 1.191 | 1.230 | 0.0672 | 0.5676 | 0.5139 | 0.0570 |
| | 14 | 1.092 | 1.138 | 1.268 | 1.230 | | 0.1680 | 0.0169 | 0.0580 | concentration levels (0, 1, 3, 5, 7, 9, 11 and 13 ppm) and three feeding durations (7, 14 or 21 days). The zilpaterol is administered in feed except for the unmediated control group. The zilpaterol treatment groups begin feeding on either 21, 28 or 35 days of age. At day 21, feeding zilpaterol occurs for either 21 or 14 days. At day 28, feeding zilpaterol occurs for either 14 or 7 days. Finally, at day 35, feeding zilpaterol begins for 7 days or longer if a larger target market weight bird is desired. Within each feed group, there are seven subgroups, one for each concentration level. For each group/subgroup, body weight and other performance characteristics are measured at the end of the feeding period as indicated.

What is claimed is:

1. A method for enhancing the performance of broiler chicken by improving one or more of the following parameters:
    increasing the average daily gain (ADG);
    decreasing the feed efficiency value (FE);
    increasing the carcass yield;
    by administering during an administration period from about 1 ppm to about 13 ppm zilpaterol in the feed to the broiler chicken wherein zilpaterol is administered every day during the zilpaterol administration period, and wherein the zilpaterol administration period either begins on 35 days of age and is for about 7 days or begins on 28 days of age and is for about 14 days.

2. The method of claim 1, wherein the zilpaterol is zilpaterol hydrochloride.

3. The method of claim 2, wherein the zilpaterol administration period begins on 35 days of age and is for about 7 days.

4. The method of claim 2, wherein the zilpaterol administration period begins on 28 days of age and is about 14 days.

5. The method of claim 1, wherein the concentration of zilpaterol is about 1 ppm.

6. The method of claim 1, wherein the concentration of zilpaterol is about 3 ppm.

7. The method of claim 1, wherein the concentration of zilpaterol is about 5 ppm.

8. The method of claim 1, wherein the concentration of zilpaterol is about 7 ppm.

9. The method of claim 1, wherein the concentration of zilpaterol is about 9 ppm.

10. The method of claim 1, wherein the concentration of zilpaterol is about 11 ppm.

11. The method of claim 1, wherein the concentration of zilpaterol is about 13 ppm.

* * * * *